United States Patent [19]

Kwiatkowski

[11]' Patent Number: 4,936,995

[45] Date of Patent: Jun. 26, 1990

[54] PHOTOCHROMIC COMPOUND AND ARTICLES CONTAINING THE SAME

[75] Inventor: Patricia L. Kwiatkowski, Akron, Ohio

[73] Assignee: PPG Industries, Inc., Pittsburgh, Pa.

[21] Appl. No.: 194,753

[22] Filed: May 17, 1988

[51] Int. Cl.$^5$ .............................................. G02B 5/23
[52] U.S. Cl. .................................... 252/586; 252/582; 544/70; 544/71
[58] Field of Search ...................... 252/582, 589, 586; 544/70, 71

[56] References Cited

U.S. PATENT DOCUMENTS

| | | | |
|---|---|---|---|
| 3,291,604 | 12/1966 | Michel et al. | 96/29 |
| 3,562,172 | 2/1971 | Ono et al. | 252/300 |
| 3,578,602 | 5/1971 | Ono et al. | 252/300 |
| 4,215,010 | 7/1980 | Hovey et al. | 252/300 |
| 4,342,668 | 8/1982 | Hovey et al. | 252/586 |
| 4,637,698 | 1/1987 | Kwak et al. | 351/163 |
| 4,719,296 | 1/1988 | Irie et al. | 544/71 |

FOREIGN PATENT DOCUMENTS

| | | |
|---|---|---|
| 1381777 | 1/1964 | France . |
| 153690 | 1/1982 | German Democratic Rep. ... 544/71 |
| 62-195075 | 8/1987 | Japan . |
| 62-195383 | 8/1987 | Japan . |
| 63-66186 | 3/1988 | Japan . |
| 63-366186 | 3/1988 | Japan . |
| 63-267784 | 11/1988 | Japan . |
| 63-267785 | 11/1988 | Japan . |
| 63-301885 | 12/1988 | Japan . |
| 63-301886 | 12/1988 | Japan . |
| 63-303984 | 12/1988 | Japan . |
| 63-305181 | 12/1988 | Japan . |
| 64-019081 | 1/1989 | Japan . |
| 64-19081 | 1/1989 | Japan . |
| WO8802371 | 4/1988 | PCT Int'l Appl. . |
| 2171404 | 4/1986 | United Kingdom . |

OTHER PUBLICATIONS

Galbershtan, M. A. et al, Khim Geterotsikl Soedin, 1976, No. 6, 815-16.

*Primary Examiner*—John F. Terapane
*Assistant Examiner*—Richard Treanor
*Attorney, Agent, or Firm*—Irwin M. Stein

[57] ABSTRACT

Described are novel spiro(benzindolino) benzoxazine compounds and compositions containing such compounds. Photochromic sprio(benzindolino) benzoxazines may be incorporated into plastic host materials to produce photochromic articles.

19 Claims, No Drawings

PHOTOCHROMIC COMPOUND AND ARTICLES CONTAINING THE SAME

DESCRIPTION OF THE INVENTION

The present invention relates to novel compounds, particularly novel photochromic compounds, and to compositions and articles containing such compounds. Photochromism is a reversible phenomenon illustrated by a compound which, when exposed to the radiation of light involving ultraviolet rays, such as sunlight or the light of a mercury lamp, changes color and then returns to its original color if the radiation is discontinued or the compound is stored in the dark.

Various types of photochromic compounds have been synthesized and suggested for use in applications in which a color change or darkening is induced by sunlight. For example, spiro(indoline) naphthoxazine compounds, as described in U.S. Pat. Nos. 3,562,172, 3,578,602, 4,215,010, 4,342,668, and UK patent application 2,171,404 are reported to be useful for sunglasses and ophthalmic lenses. Other photochromic compounds reported to be useful in ophthalmic applications are spiro(indoline) pyrido benzoxazines, which are described in U.S. Pat. No. 4,637,698. Such photochromic compounds either in crystalline form, or in solution or dispersed in a transparent medium change from a colorless state to blue when exposed to sunlight or ultraviolet radiation, and return to their original colorless state when such radiation is removed.

DETAILED DESCRIPTION OF THE INVENTION

In accordance with the present invention, there are provided novel spiro (benzindolino) benzoxazine compounds, which may be represented by the following graphic formula I,

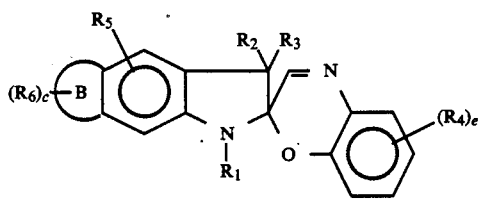

(I)

Ring B represents a substituted or unsubstituted benzene ring fused to the six membered ring of the indolino portion of the depicted formula. Ring B may be fused at the e, f, or g face of the indoline portion of the compound. Preferably, ring B is fused at the e face, as represented respectively by graphic formula IA:

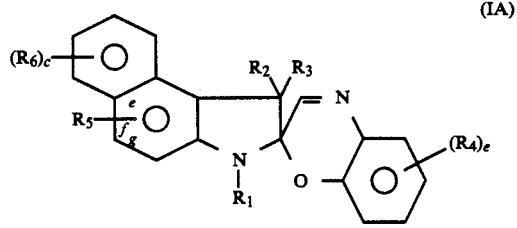

(IA)

When ring B is fused at the e face, the compounds are numbered as depicted in graphic formula IA'. When ring B is fused at the g face, the compounds are numbered as depicted in graphic formula IB.

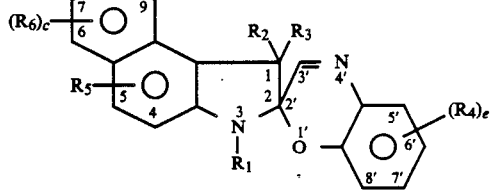

(IA')

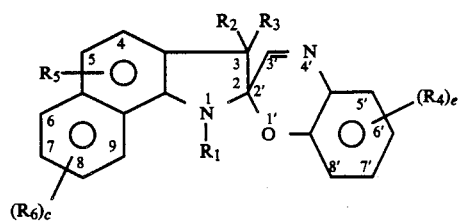

(IB)

In the above graphic formulae, $R_1$ is selected from the group consisting of $C_1$–$C_8$ alkyl, e.g., methyl, ethyl, propyl, butyl, etc., phen($C_1$–$C_4$)alkyl, e.g. benzyl, naphth($C_1$–$C_4$)alkyl, e.g., 1-naphthylmethyl, allyl, acrylyl, methacrylyl, carboxy($C_2$–$C_6$)alkyl, e.g., β-carboxyethyl, γ-carboxypropyl and δ-carboxybutyl, cyano ($C_2$–$C_6$)alkyl, e.g., β-cyanoethyl, γ-cyanopropyl, β-cyanoisopropyl and δ-cyanobutyl, $C_1$–$C_4$ acyloxy($C_2$–$C_6$) alkyl, i.e., [$R_c$C(O)$R_d$-, wherein $R_c$ is a $C_1$–$C_4$ alkyl and $R_d$ is a $C_2$–$C_6$ alkyl], e.g.. acetoxyethyl, acetoxypropyl, propionyloxyethyl, acetoxybutyl and propionyloxypropyl, hydroxy($C_2$–$C_6$)alkyl, e.g., hydroxyethyl, hydroxypropyl and hydroxybutyl, and ($C_2H_4O$)$_m$·$CH_3$, wherein m is a number of from 1 to 6. Preferably, $R_1$ is $C_1$–$C_4$ alkyl, allyl, ($C_2H_4O$)$_m$·$CH_3$, wherein m is a number of from 1 to 3, e.g., 2, carboxy($C_2$–$C_4$)alkyl, cyano($C_2$–$C_4$)alkyl, e.g., cyanoethyl, $C_1$–$C_4$ acyloxy ($C_2$–$C_4$)alkyl, e.g., $C_2$–$C_4$ acyloxyethyl, and hydroxy($C_2$–$C_4$)alkyl.

$R_2$ and $R_3$ of formula I are each selected from the group consisting of $C_1$–$C_5$ alkyl, phenyl, mono- and di-substituted phenyl and phen($C_1$–$C_4$)alkyl, e.g., benzyl, or $R_2$ and $R_3$ may combine to form an alicyclic ring containing from 6 to 8 carbon atoms (including the spiro carbon atom). The aforesaid phenyl substituents may be selected from $C_1$–$C_5$ alkyl and $C_1$–$C_5$ alkoxy groups. More particularly, $R_2$ and $R_3$ are each selected from $C_1$–$C_5$ alkyl, e.g., methyl, ethyl, propyl, butyl, and pentyl, and phenyl. When one of $R_2$ or $R_3$ is a tertiary alkyl radical, such as tertiary butyl or tertiary amyl, the other is preferably an alkyl radical other than a tertiary alkyl radical.

$R_4$ in graphic formula I may be selected from the group consisting of halogen, e.g., chloro, fluoro or bromo, $C_1$–$C_5$ alkyl, $C_1$–$C_5$ alkoxy. e.g., methoxy, ethoxy, propoxy, butoxy and pentoxy, nitro, cyano, thiocyano, $C_1$–$C_4$ monohaloalkyl, e.g., $C_1$–$C_4$ monochloroalkyl such as chloromethyl and chloroethyl, $C_1$–$C_2$ polyhaloalkyl, as for example trihaloalkyl such as trichloro- or trifluoroalkyl, e.g., trifluoromethyl and 1,1,1-trifluoroethyl, and mono- or dialkylamino wherein the alkyl moiety of the alkylamino group contains from 1 to 4 carbon atoms, e.g, methylamino, ethylamino, propylamino, dimethylamino or diethylamino. The letter "e" in formula I is an integer of from 1 to 4, usually 1, 2, or 3, and preferably 1 or 2. In particular, each $R_4$ substituent may be selected from the group $C_1$-$C_2$ alkyl, $C_1$-$C_2$ alkoxy, chloro, fluoro, bromo, nitro, trifluoromethyl and dimethylamino.

When "e" is 1, the $R_4$ substituent may be located on any of the available carbon atoms of the benzene ring of the benzoxazine moiety of the compound, i.e., at the 5', 6', 7' or 8' positions. Preferably, the $R_4$ substituent is present on the 5', 6' or 7' carbon atoms of the benzene ring of the benzoxazine moiety. When "e" is 2 or more, the $R_4$ substituents may be the same or different and in either case are selected from the above-described group. When "e" is 2, the $R_4$ substituents are typically located at the 5' and 7' or 6' and 8' positions. When "e" is 3, the $R_4$ substituents are typically located at the 5', 6', and 7'; 5', 7', and 8'; 6', 7', and 8'; or 5', 6', and 8' positions.

$R_5$ in graphic formula I is selected from the group consisting of hydrogen, halogen, e.g., chloro, fluoro or bromo, $C_1$-$C_5$ alkyl, e.g., $C_1$-$C_2$ alkyl, $C_1$-$C_5$ alkoxy, e.g., $C_1$-$C_2$ alkoxy, $C_1$-$C_4$ monohaloalkyl, e.g., $C_1$-$C_2$ monohaloalkyl such as chloromethyl, chloroethyl and fluoromethyl, $C_1$-$C_2$ polyhaloalkyl, as for example, trihaloalkyl such as trichloro- or trifluoroalkyl, e.g., trifluoromethyl, cyano and $C_1$-$C_8$ alkoxycarbonyl. The $R_5$ substituent may be located at either the number 4 or 5 carbon atom positions. In particular, $R_5$ is selected from $C_1$-$C_2$ alkyl, $C_1$-$C_2$ alkoxy, $C_1$-$C_2$ monohaloalkyl, hydrogen, fluoro and trifluoromethyl.

$R_6$ in graphic formula I is selected from the group consisting of halogen, e.g., chloro, fluoro or bromo, $C_1$-$C_5$ alkyl, e.g., $C_1$-$C_2$ alkyl, $C_1$-$C_5$ alkoxy, e.g., $C_1$-$C_2$ alkoxy, cyano. $C_1$-$C_8$ alkoxycarbonyl, $C_1$-$C_2$ polyhaloalkyl, $C_1$-$C_4$ monohaloalkyl and mono- or dialkylamino, wherein the alkyl moiety of the alkylamino group contains from 1 to 4 carbon atoms, e.g., methylamino, ethylamino, propylamino and diethylamino.

The letter "c" in formula I is an integer of from 0 to 2, e.g., 0 or 1, more typically 0. When there are substituents on the benz moiety of the benzindolino portion of the compound and the letter "c" is 1 or 2, it denotes the number of non-hydrogen substituents. When "c" is 1, the $R_6$ substituent is typically located at the number 6, 7 or 8 carbon atom. Similarly, when "c" is 2, the $R_6$ substituents are usually present at the 6 and 7, 6 and 8, or 7 and 8 carbon atoms.

Of particular interest, are compounds represented by graphic formula IA, wherein $R_1$ is a $C_1$-$C_4$ alkyl, such as methyl, ethyl, n-propyl, isopropyl, n-butyl, secondary butyl, isobutyl and tertiary butyl; $R_2$ and $R_3$ are each methyl, ethyl or phenyl; $R_4$ is selected from $C_1$-$C_4$ alkyl, $C_1$-$C_4$ alkoxy, chloro, fluoro or cyano; $R_5$ is selected from hydrogen, fluoro, trifluoromethyl and $C_1$-$C_5$ alkyl; $R_6$ is selected from $C_1$-$C_5$ alkyl, trifluoromethyl, $C_1$-$C_5$ alkoxy, chloro, fluoro and $C_1$-$C_4$ mono- or dialkylamino; "c" is 0 or 1; and "e" is 1 or 2.

Examples of contemplated compounds within the scope of graphic formula I, particularly IA, are listed in Table I. The prime (') designations for the $R_4$ substituent positions in Table I have been omitted. Compound 1 of Table I may be named: 5',7'-dimethoxy-1,1,3-trimethyl-spiro[benz[e]indoline-2,2'-[2H-1,4]benzoxazine]. Usually, the $R_4$ substituent (when "e" is 1) will be located at the 5' or 7' carbon atom, usually at the 7' carbon atom. When "e" is 2, the $R_4$ substituents will usually be located at the 5' and 7' carbon atoms. For example, in Table I, the recited monomethoxy (OMe) and monoethoxy (OEt) substituents will commonly be a 7'-methoxy or 7'-ethoxy substituent. The dimethoxy substituents of compounds 1-12, 18 and 23-25 will commonly be 5', 7'-dimethoxy substituents. The bromo substituent of compound 22 may be a 7'-bromo substituent. Compounds represented in Table I may be named similarly to compound 1 as substituted spiro benz(indolino) benzoxazines using the substituents described in the Table for such compounds. In naming such compounds herein, the IUPAC rules of organic nomenclature have been used. Carbon atom numbering in the compounds is in accordance with the numbering sequence illustrated in graphic formulae IA' and IB.

TABLE I

| Compound No. | $R_1$ | $R_2$ | $R_3$ | $R_4$ | $R_5$ | $R_6$ | Face |
|---|---|---|---|---|---|---|---|
| 1 | Me | Me | Me | (OMe)$_2$ | H | — | e |
| 2 | Me | Me | Me | (OMe)$_2$ | H | — | g |
| 3 | Et | Me | Me | (OMe)$_2$ | H | — | e |
| 4 | n-Pr | Me | Me | (OMe)$_2$ | H | — | e |
| 5 | i-Pr | Me | Me | (OMe)$_2$ | H | — | e |
| 6 | Et | Me | Me | (OMe)$_2$ | H | — | g |
| 7 | n-Pr | Me | Me | (OMe)$_2$ | H | — | g |
| 8 | Me | Me | Me | (OMe)$_2$ | F | — | e |
| 9 | Me | Me | Me | (OMe)$_2$ | CF$_3$ | — | e |
| 10 | Me | Me | Me | (OMe)$_2$ | F | — | g |
| 11 | Me | Me | Me | (OMe)$_2$ | CF$_3$ | — | g |
| 12 | Me | Me | Ph | (OMe)$_2$ | H | Cl | g |
| 13 | Me | Me | Me | OMe | — | — | g |
| 14 | Et | Me | Me | (NEt$_2$)(OMe) | F | — | e |
| 15 | Me | Me | Me | OMe | Me | Me | e |
| 16 | Me | Me | Me | NO$_2$ | CF$_3$ | — | g |
| 17 | Me | Me | Me | Cl | H | — | e |
| 18 | Me | Me | Me | (OMe)$_2$ | CH$_3$C(O)— | — | g |
| 19 | Me | Me | Me | OMe | H | Cl | e |
| 20 | Me | Me | Me | OEt | H | — | e or g |
| 21 | Me | Me | Me | Br | H | — | e or g |
| 22 | (CH$_2$)$_3$CN | Me | Me | (OMe)$_2$ | H | — | e or g |
| 23 | (CH$_2$)$_2$COOH | Me | Me | (OMe)$_2$ | H | — | e or g |

TABLE I-continued

SUBSTITUENT

| Compound No. | R$_1$ | R$_2$ | R$_3$ | R$_4$ | R$_5$ | R$_6$ | Face |
|---|---|---|---|---|---|---|---|
| 24 | (CH$_2$)$_2$OH | Me | Me | (OMe)$_2$ | H | — | e or g |

Key for Table
Me = methyl
Et = ethyl
n-Pr = n-propyl
i-Pr = isopropyl
(CH$_2$)$_3$CN = cyanopropyl
(CH$_2$)$_2$COOH = carboxyethyl
Ph = phenyl
OMe = methoxy
OEt = ethoxy
NO$_2$ = nitro
NEt$_2$ = diethylamino
(CH$_2$)$_2$OH = hydroxyethyl
CF$_3$ = trifluormethyl
Cl = chlorine
F = fluorine
Br = bromine
CH$_3$C(O) = acetoxy
A hyphen (-) denotes the absence of non-hydrogen substituents.

The compounds of the present invention may be synthesized by reaction of the corresponding R$_5$ and (R$_6$)$_c$—substituted indoline (Fischer's base) or indolium salt, e.g., the iodide salt, with the corresponding (R$_4$)$_c$- substituted-1-nitroso-2-phenol. These precursor materials may be reacted in substantially stoichiometric amounts in a suitable solvent, such as toluene or ethanol at temperatures of from about 40° C. to about 140° C., more usually from 40° C. to 120° C., until the reaction is completed. When the indolium salt is used, a base, such as triethylamine or piperidine, is incorporated into the reaction medium to combine with the hydrogen halide liberated during the reaction.

Any common organic solvent (polar and non-polar) except for low boiling aliphatic hydrocarbon solvents, such as pentane, may be used as the reaction medium. Contemplated as suitable solvents are alcohols such as C$_1$-C$_4$ alkanols, e.g., methanol, ethanol, isopropanol, and the butanols; aromatic solvents such as benzene, toluene and xylene; ketones such as acetone, methyl ethyl ketone and methyl isobutyl ketone; esters such as ethyl acetate; chlorinated lower aliphatic hydrocarbons such as methylene chloride and chloroform; dimethylsulfoxide, dimethylformamide, tetrahydrofuran; and mixtures of C$_1$-C$_4$ alkanols and aliphatic hydrocarbon solvents such as ethanol-hexane and ethanol-heptane mixtures.

While reaction temperatures below 40° C. may be used, the reaction rate is very slow and inefficient. Reaction temperatures above 120° C. may cause decomposition of the product. Hence, temperatures of from 40° C. to 120° C., e.g., 50° C. to 100° C. are considered most suitable. Stirring of the reaction medium at elevated reaction temperatures within the aforesaid ranges is recommended to prevent decomposition of the product.

An organic or inorganic base may be used to react with the hydrogen halide that is liberated during the reaction as a result of using an indolium halide salt reactant. Amines such as trimethylamine, triethylamine, diisopropylamine, piperidine, pyridine and piperazine may be used. Inorganic basic reagents such as sodium carbonate, sodium bicarbonate, potassium hydroxide, sodium hydroxide and sodium acetate may be used. The use of inorganic reagents will entail a two-phase reaction medium, i.e., an inorganic and organic phase. The basic reagent is commonly used in a stoichiometric excess, although stoichiometric amounts may be used.

The reaction product is recovered from the reaction mixture, e.g., by filtration or decanting - depending on whether the product is a solid or liquid. The product may be purified by flash column chromatography, crystallization, boiling with carbon black or other techniques known in the art.

More particularly, the compounds of the present invention may be prepared by reacting one equivalent of the corresponding substituted Fischer's base hydroiodide salt with one equivalent of the corresponding substituted nitrosophenol in an ethanol solution containing an excess of triethylamine. The liquid reaction mixture is heated to 70° C. and maintained at about that temperature for about 5 hours. The progress of the reaction may be monitored by thin layer chromatography (TLC). The ethanol solvent and excess triethylamine are evaporated and the residue purified by column chromatography using ethylacetate and hexane as eluents, or by recrystallization from appropriate solvents.

Still more particularly, one equivalent of 3,5-dimethoxy-2nitrosophenol may be condensed with one equivalent of 1,2,3,3-tetramethyl benz(e) indoline. A suspension of the indoline and the nitrosophenol in ethanol may be refluxed under nitrogen until the condensation reaction has been completed, e.g., 2 to 6 hours. The resulting spiro benz[e](indolino) benzoxazine, i.e., is compound 1 in Table I.

The R$_5$ and (R$_6$)$_c$- substituted indoline (or indolium salt) may be prepared by converting the corresponding R$_5$- and (R$_6$)$_c$- substituted naphthylamine to the corresponding hydrazine hydrochloride by conventional synthesis procedures. See, for example. R. K. Brown, "The Chemistry of Heterocyclic Compounds", Wiley Interscience, New York, Volume 25, Part I, Chapter 2, page 232.

The hydrazine hydrochloride may be condensed with the required ketone by reaction of stoichiometric amounts of the reagents in glacial acetic acid at 100° C. or in refluxing ethanol to form the corresponding (3H)indole. The (3H)indole may be converted to the Fischer's base hydroiodide salt by alkylation with excess alkyl iodide under reflux conditions.

The compounds of the present invention may be dissolved in common organic solvents such as benzene, toluene, chloroform, ethylacetate, methylethylketone, acetone, ethyl alcohol, methyl alcohol, acetonitrile, tetrahydrofuran, dioxane, methyl ether of ethylene glycol, dimethylformamide, dimethylsulfoxide, methyl Cellosolve, morpholine and ethylene glycol. The compounds can also be dispersed in liquids containing water, alcohols and other solvents.

The compounds of the present invention may also be dissolved in colorless or transparent solutions prepared from transparent organic host materials, e.g., transparent polymers (or copolymers) or blends of such transparent polymers and optionally a suitable organic solvent, e.g., polymers of transparent organic host materials described hereinafter dissolved in one or more of the aforesaid described organic solvents. Examples of such solutions include a poly(vinyl acetate)-acetone solution, a nitrocellulose-acetonitrile solution, a poly(vinyl chloride)-methylethylketone solution, a poly(methylmethacrylate)-acetone solution, a cellulose acetate-dimethylformamide solution, a poly(vinyl pyrrolidone)-acetonitrile solution, a polystyrene-benzene solution and an ethyl cellulose-methylene chloride solution. The aforesaid solutions or compositions of compounds wherein ring B is fused at the e face may be applied to a compatible host material, e.g., a transparent support, such as cellulose triacetate and polyethylene terephthalate, or baryta paper and dried to obtain an article that may be color formed by ultraviolet radiation and returned to a colorless state by removing the source of ultraviolet radiation. Compounds wherein ring B is fused at the g face exhibit less photochromism than those wherein ring B is fused at the e face. See figure IA.

In an embodiment of the present invention, the compounds described herein (or compositions containing them) may be applied to or incorporated within a coating composition applied to a compatible host; or applied to or incorporated within the article comprising the compatible host, e.g., a polymerized organic material such as a synthetic plastic host material. In one embodiment, the host material article is a solid transparent material or an optically clear material, e.g., materials suitable for ophthalmic elements, such as ophthalmic lenses, or materials useful for applications such as windows, windshields, etc. A host material containing photochromic compounds of the present invention may be used in the preparation of photochromic plastic films, sheets and lenses, such as lenses for sunglasses, ski goggles, visors, camera lenses and variable density filters. As used herein, the term "optical element" is meant to include lenses and transparencies. The photochromic materials of the present invention also may be incorporated into coatings such as paints, inks, etc. by admixing the material with the fluid coating composition before it is applied to the host surface and dried.

Examples of host materials that may be used with the photochromic compounds of the present invention include: polymers, i.e., homopolymers and copolymers, of polyol(allyl carbonate) monomers, homopolymers and copolymers of polyfunctional acrylate monomers, polyacrylates, poly(alkylacrylates) such as poly(methylmethacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polycarbonates, poly(ethylene-terephthalate), polystyrene, copoly(styrene-methylmethacrylate), copoly(styrene-acrylonitrile), poly(vinylbutyral), and homopolymers and copolymers of diallylidene pentaerythritol, particularly copolymers with polyol (allyl carbonate) monomers, e.g., diethylene glycol bis(allyl carbonate), and acrylate monomers. Transparent copolymers and blends of the transparent polymers are also suitable as host materials.

Preferably, the host material is an optically clear polymerized organic material prepared from a polycarbonate resin, such as the carbonate-linked resin derived from bisphenol A and phosgene, which is sold under the trademark, LEXAN; a poly(methylmethacrylate), such as the material sold under the trademark, PLEXIGLAS; polymerizates of a polyol(allyl carbonate), especially diethylene glycol bis(allyl carbonate), which monomer is sold under the trademark CR-39, and its copolymers such as copolymers with vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate; cellulose acetate, cellulose propionate, cellulose butyrate, polystyrene and copolymers of styrene with methyl methacrylate, vinyl acetate and acrylonitrile, and cellulose acetate butyrate.

Polyol (allyl carbonate) monomers which can be polymerized to form a transparent host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g, glycols. The monomers can be prepared by Procedures well known in the art, e.g., U.S. Pat. Nos. 2,370,567 and 2,403,113.

The polyol (allyl carbonate) monomers can be represented by the graphic formula:

(II)

wherein R is the radical derived from an unsaturated alcohol and is commonly an allyl or substituted allyl group, R' is the radical derived from the polyol, and n is a whole number from 2–5, preferably 2. The allyl group (R) can be substituted at the 2 position with a halogen, most notably chlorine or bromine, or an alkyl group containing from 1 to 4 carbon atoms, generally a methyl or ethyl group. The R group can be represented by the graphic formula:

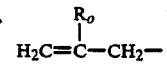

wherein $R_o$ is hydrogen, halogen, or a $C_1$–$C_4$ alkyl group. Specific examples of R include the groups: allyl, 2-chloroallyl, 2-bromoallyl, 2-fluoroallyl, 2-methallyl, 2-ethylallyl, 2-isopropylallyl, 2-n-propylallyl, and 2-n-butylallyl. Most commonly R is the allyl group. $H_2C=CH-CH_2-$.

R' is a polyvalent radical derived from the polyol, which can be an aliphatic or aromatic polyol that contains 2, 3, 4 or 5 hydroxy groups. Typically, the polyol contains 2 hydroxy groups, i.e., a glycol or bisphenol. The aliphatic polyol can be linear or branched and contain from 2 to 10 carbon atoms. Commonly, the aliphatic polyol is an alkylene glycol having from 2 to 4 carbon atoms or a poly($C_2$–$C_4$) alkylene glycol, i.e., ethylene glycol, propylene glycol, trimethylene glycol, tetramethylene glycol, or diethylene glycol, triethylene glycol, etc.

The aromatic polyol may be represented by the graphic formula:

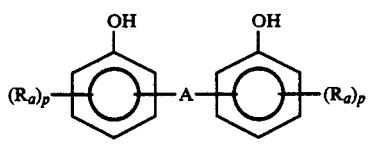 (III)

wherein A is a bivalent radical derived from an acyclic aliphatic hydrocarbon, e.g., an alkylene or alkylidene radical, having from 1 to 4 carbon atoms, e.g., methylene, ethylene, and dimethylmethylene (isopropylidene:), Ra represents lower alkyl substituents of from 1 to 3 carbon atoms, and p is 0, 1, 2, or 3. Preferably, the hydroxyl group is in the ortho or para position.

Specific examples of the radical R' include: alkylene groups containing from 2 to 10 carbon atoms such as ethylene, (—CH$_2$—CH$_2$—), trimethylene, methylethylene, tetramethylene, ethylethylene, pentamethylene, hexamethylene, 2-methylhexamethylene, octamethylene, and decamethylene; alkylene ether groups such as —CH$_2$—O—CH$_2$—. —CH$_2$CH$_2$—O—CH$_2$CH$_2$—, —CH$_2$—O—CH$_2$—CH$_2$—, and —CH$_2$CH$_2$CH$_2$—O—CH$_2$CH$_2$CH$_2$—; alkylene polyether groups such as —CH$_2$CH$_2$—O—CH$_2$CH$_2$—O—CH$_2$CH$_2$—, and —CH$_2$CH$_2$CH$_2$—O—CH$_2$CH$_2$CH$_2$—; alkylene carbonate and alkylene ether carbonate groups such as —CH$_2$CH$_2$—O—CO—O—CH$_2$CH$_2$— and —CH$_2$CH$_2$—O—CH$_2$CH$_2$—O—CO—O—CH$_2$CH$_2$—O—CH$_2$CH$_2$—;and isopropylidene bis(para-phenyl), i.e.,

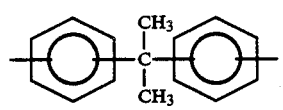 (IV)

Most commonly, R' is —CH$_2$CH$_2$—, —CH$_2$CH$_2$—O—CH$_2$CH$_2$—, or —CH$_2$CH$_2$—O—CH$_2$CH$_2$—O—CH$_2$CH$_2$—.

Specific examples of polyol (allyl carbonate) monomers include ethylene glycol bis(2-chloroallyl carbonate), ethylene glycol bis(allyl carbonate), diethylene glycol bis(2-methallyl carbonate), diethylene glycol bis(allyl carbonate), triethylene glycol bis(allyl carbonate), propylene glycol bis(2-ethylallyl carbonate), 1,3-propanediol bis(allyl carbonate), 1,3-butanediol bis(allyl carbonate), 1,4-butanediol bis(2-bromoallyl carbonate), dipropylene glycol bis(allyl carbonate), trimethylene glycol bis(2-ethylallyl carbonate), pentamethylene glycol bis(allyl carbonate), and isopropylidene bisphenol bis(allyl carbonate).

Industrially important polyol bis(allyl carbonate) monomers which can be utilized in the invention herein contemplated are:

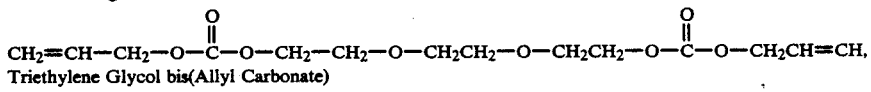 (V)
Triethylene Glycol bis(Allyl Carbonate)

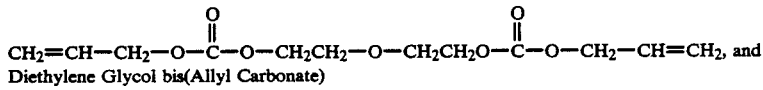 (VI)
Diethylene Glycol bis(Allyl Carbonate)

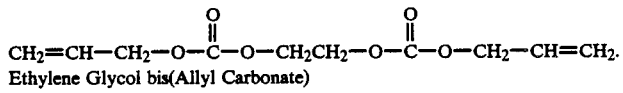 (VII)
Ethylene Glycol bis(Allyl Carbonate)

Diethylene glycol bis(allyl carbonate) is preferred.

Because of the process by which the polyol(allyl carbonate) monomer is prepared, i.e., by phosgenation of the polyol (or allyl alcohol) and subsequent esterification by the allyl alcohol (or polyol), the monomer product can contain related monomer species in which the moiety connecting the ally carbonate groups contains one or more carbonate groups. These related monomer species can be represented by the graphic formula:

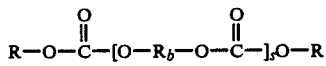 (VIII)

wherein R is as defined above, R$_b$ is a bivalent radical, e.g., alkylene or phenylene, derived from a diol, and s is a whole number from 2 to 5. The related monomer species of diethylene glycol bis(allyl carbonate) can be represented by the graphic formula,

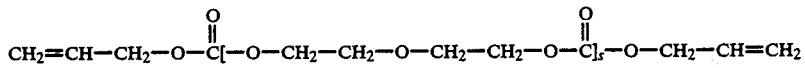 (IX)

wherein s is a whole number from 2 to 5. The polyol (allyl carbonate) monomer can typically contain from 2 to 20 weight percent of the related monomer species and such related monomer species can be present as mixtures, i.e., mixtures of the species represented by s being equal to 2, 3, 4 etc.

In addition, a partially polymerized form of the polyol (allyl carbonate) monomer can be used. In that embodiment, the monomer is thickened by heating or partially polymerized by using small, e.g., 0.5–1.5 parts of initiator per hundred parts of monomer (phm), to provide a non-gel containing, more viscous monomeric material.

As used in the present description and claims, the term polyol(allyl carbonate) monomer or like names, e.g., diethylene glycol bis(allyl carbonate), are intended to mean and include the names monomer or prepolymer and any related monomer species contained therein.

Polyfunctional acrylate monomers that may be used to prepare synthetic polymeric host materials are esterification products of an acrylic acid moiety selected from the group consisting of acrylic acid and methacrylic acid, and a polyol, e.g., a diol, a triol or tetracarbinol. More particularly, the polyfunctional acrylate monomer may be represented by the following graphic formula:

$$(CH_2=C(R_t)-C(O))_{\overline{n}}R'' \qquad (X)$$

wherein $R_t$ is hydrogen or methyl, n is the number 2, 3, or 4, and R: is the multivalent radical, i.e., a bivalent, trivalent or quadrivalent radical, remaining after removal of the hydroxy groups from a polyol, having from 2 to 4 hydroxy groups, e.g., a diol, a triol or tetracarbinol respectively. More particularly, $R_t$ is hydrogen or methyl, and n is 2 or 3, more usually 2.

R'' may be selected from the group consisting of alpha, omega $C_2$-$C_8$ glycols, cyclohexane diol, diethylene glycol, triethylene glycol, tetraethylene glycol, dipropylene glycol, $C_2$-$C_5$ triols and pentaerythritol. Examples of such polyols include ethylene glycol, trimethylene glycol, 1,4-butane diol, 1,5-pentane diol, 1,6-hexane diol, propylene glycol, trimethylol propane, glycerol and the like.

Examples of polyfunctional acrylate monomers, such as diacrylates and triacrylates, include: ethylene glycol diacrylate, ethylene glycol dimethacrylate, 1,2-propane diol diacrylate, 1,3-propane diol diacrylate, 1,2-propane diol dimethacrylate, 1,3-propane diol dimethacrylate, 1,4-butane diol diacrylate, 1,3-butane diol dimethacrylate, 1,4-butane diol dimethacrylate, 1,5-pentane diol diacrylate, 2,5-dimethyl-1,6-hexane diol dimethacrylate, diethylene glycol diacrylate, diethylene glycol dimethacrylate, triethylene glycol dimethacrylate, trimethylol propane trimethacrylate, tetraethylene glycol diacrylate, tetraethylene glycol dimethacrylate, dipropylene glycol diacrylate, dipropylene glycol dimethacrylate, trimethylol propane triacrylate, glycerol triacrylate, glycerol trimethacrylate, pentaerythritol triacrylate, pentaerythritol dimethacrylate, pentaerythritol tetraacrylate, pentaerythritol tetramethacrylate and mixtures of such acrylate monomers.

A portion of the polyfunctional acrylate monomer may be replaced with a monofunctional copolymerizable monomer containing the vinyl ($CH_2=CH-$) grouping. Such compatible monomers include monofunctional acrylic and methacrylic acid esters, and vinyl esters of $C_2$-$C_6$ carboxylic acids, i.e., vinyl carboxylates. Preferably, the copolymerizable monomer is a non-aromatic, e.g., non-benzoid, containing monomer. Monofunctional acrylic or methacrylic ester monomers may be graphically illustrated by the following formula, $$CH_2=C(R_t)-C(O)-O-R''' \qquad (XI)$$

wherein $R_t$ is hydrogen or methyl, and R''' is selected from the group consisting of $C_1$-$C_{12}$, e.g., $C_1$-$C_8$ alkyl, $C_5$-$C_6$ cycloalkyl, glycidyl and hydroxyethyl. Preferably, R''' is a $C_1$-$C_4$- alkyl, e.g., methyl or cyclohexyl.

Examples of monofunctional acrylic acid type monomers include, for example, the acrylic and methacrylic acid esters of alkanols such as methanol, ethanol, propanol, butanol, pentanol, hexanol, heptanol and octanol, e.g., methyl acrylate, methyl methacrylate, ethyl acrylate and ethyl methacrylate, cycloalkanols such as cyclopentanol and cyclohexanol, glycidol (3-hydroxy propylene oxide, (d, 1, dl)) and ethylene glycol. Examples of vinyl carboxylates include vinyl acetate, vinyl propionate, vinyl butyrate and vinyl valerate. In addition to and/or in place of the aforedescribed monofunctional copolymerizable monomer, monofunctional allylic and difunctional allylic copolymerizable compatible monomers may also replace a portion of the polyfunctional acrylate monomer. Monofunctional allylic monomers contemplated include allyl esters of $C_2$-$C_6$ carboxylic acids, $C_1$-$C_6$ allyl ethers and other copolymerizable allyl compounds. Preferably the monofunctional allylic monomer is a non-aromatic compound. Difunctional allylic copolymerizable monomers contemplated herein are the polyol (allyl carbonates) monomers of graphic formula VI.

The amount of photochromic compound or composition-containing same applied to or incorporated into a host material is not critical provided that a sufficient amount is used to produce a photochromic effect discernible to the naked eye. Generally such amount can be described as a photochromic amount. The amount used depends often upon the intensity of color desired upon irradiation thereof and upon the method used to incorporate or apply the photochromic compound. Typically, the more compound applied or incorporated, the greater is the color intensity. Usually, the amount of photochromic compound incorporated into or applied to the host material ranges from about 0.01 to about 20 percent by weight, more usually from about 0.05 to about 10 percent by weight, based on the weight of the host material. Stated another way, the amount of photochromic compound used to impart a photochromic effect will typically vary from about 1 to about 50, e.g., 1 to 10 milligrams of the photochromic compound per square inch of the surface of the host material independent of the thickness of the host material article. Hence, the photochromic compound is present in higher concentrations in thin samples, films, or coatings, and in lower concentrations in thick samples.

Solutions of the photochromic compounds of the present invention undergo a change in color upon exposure to ultraviolet radiation and return to their original color or colorless state upon removal of the source of ultraviolet radiation. Such color change may be repeated numerous times.

The photochromic compounds (or compositions containing same) of the present invention may be applied to or incorporated into a host material by methods known in the art. Such methods include dissolving or dispersing the compound in the host material, i.e., imbibation of the photochromic compound into the host material, by immersion, thermal transfer, or coating, and incorporation of the photochromic compound as part of a separate layer between adjacent layers of the host material. The term "imbibation" or "imbibe" is intended to mean and include diffusion of the photochromic compound alone into the host material, solvent assisted diffusion, absorption of the photochromic compound into a porous polymer, vapor phase transfer, and other such transfer mechanisms. For example:

(a) The photochromic compounds (or compositions containing same) of the present invention can be mixed with a polymerizable composition that, upon curing, produces an optically clear polymeric host material and the polymerizable composition cast as a film, sheet or lens, or injection molded or otherwise formed into a sheet or lens;

(b) The photochromic compounds of the present invention can be dissolved or dispersed in water, alcohol or other solvents or solvent mixtures and then imbibed into the solid host material by immersion for from several minutes to several hours, e.g., 2-3 minutes to 2-3 hours of the host material in a bath of such solution or dispersion. The bath is conventionally at an elevated temperature, usually in the range of 50° C.–120° C. Thereafter, the host material is removed from the bath and dried;

(c) The photochromic compounds (and compositions containing same) may also be applied to the surface of the host material by any convenient manner, such as spraying, brushing, spin-coating or dip-coating from a solution or dispersion of the photochromic material in the presence of a polymeric binder. Thereafter, the photochromic compound is imbibed by the host material by heating it, e.g, in an oven, for from a minute to several hours at temperatures in the range of from 80–180° C.;

(d) In a variation of the above imbibation procedure, the photochromic compound or composition containing same can be deposited onto a temporary support, e.g., a sheet of kraft paper, aluminum foil, polymer film or fabric, which is then placed in contact with the host material and heated, e.g., in an oven;

(e) The photochromic compounds can be dissolved or dispersed in a transparent polymeric material which can be applied to the surface of the host in the form of a permanent adherent film or coating by any suitable technique such as spraying, brushing, spin-coating or dip-coating; and (f) Finally, the photochromic compounds can be incorporated or applied to a transparent polymeric material by any of the above-mentioned methods, which can then be placed within the host material as a discrete layer intermediate to adjacent layers of a host material(s).

The present invention is more particularly described in the following examples which are intended as illustrative only since numerous modifications and variations therein will be apparent to those skilled in the art.

EXAMPLE 1

To 6.05 grams of 1,2,3,3-tetramethyl benz[g]indolium iodide in 30 milliliters (ml) of hexane and 30 ml of absolute ethanol under nitrogen and at room temperature is added 2.0 grams of triethyl amine in one portion. The resultant homogeneous solution is heated to mild reflux and 2.53 grams of solid 3,5-dimethoxy-2-nitrosophenol added portionwise over 20 minutes. The solution is stirred at reflux for 4 hours and then cooled overnight while being stirred. The solvent is removed under vacuum and the reaction mixture purified by column chromatography to give 0.24 grams of the desired reaction product as a pale colored solid. The product, i.e., 5'7'-dimethoxy-1,3,3-trimethylspiro[benz[g]indolino-2,2'-[2H-1,4]benzoxazine], was characterized by appropriate spectral techniques.

EXAMPLE 2

To 3.51 grams of 1,1,2,3-tetramethyl benz[e]indolium iodide in 35 ml of absolute ethanol under nitrogen at room temperature is added 1.5 grams triethylamine in one portion. The resultant homogeneous solution is heated to mild reflux and 2.75 grams of solid 3,5-dimethoxy-2-nitrososphenol added in one portion. The solution is stirred at reflux for 3½ hours, cooled to room temperature, and the solvent removed under vacuum. The reaction mixture is purified by column chromatography to yield 1.32 grams of the desired reaction product as a yellow solid. The product, i.e., 5'7'-dimethoxy-1,1,3-trimethylspiro[benz[e]indolino-2,2'-[2H-1,4]ben-zoxazine], was characterized by appropriate spectral techniques.

Although the present invention has been described with reference to specific details of certain embodiments thereof, it is not intended that such detail should be regarded as limitation upon the scope of the invention except as and to the extent that they are included in the accompanying claims.

What is claimed is:

1. A compound represented by the following graphic formula:

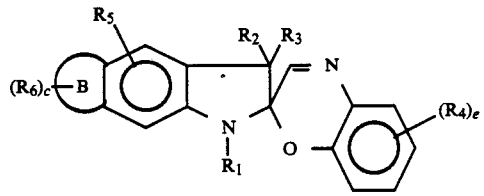

wherein:
(i) B is a benzene ring that is fused to the e, f, or g face of the six member ring of the indolino portion of the compound, (ii) $R_1$ is selected from the group consisting of $C_1$–$C_8$ alkyl, phen($C_1$–$C_4$) alkyl, naphth($C_1$–$C_4$)alkyl, allyl, acrylyl, methacrylyl, carboxy($C_2$–$C_6$)alkyl, cyano($C_2$–$C_6$)alkyl, $C_1$–$C_4$ acyloxy($C_2$–$C_6$)alkyl, hydroxy($C_2$–$C_6$)alkyl, and $(C_2H_4O)_m \cdot CH_3$, wherein m is an integer of from 1 to 6;

(iii) $R_2$ and $R_3$ are each selected from the group consisting of $C_1$–$C_5$ alkyl, phenyl, mono- and di- substituted phenyl, and phen($C_1$–$C_4$) alkyl, or combine to form an alicyclic ring containing from 6 to 8 carbon atoms (including the spiro carbon atom), said phenyl substituents being selected from $C_1$–$C_5$ allyl and $C_1$–$C_5$ alkoxy;

(iv) each $R_4$ is selected from the group consisting of halogen, $C_1$–$C_5$ alkyl, $C_1$–$C_5$ alkoxy, nitro, cyano, thiocyano, $C_1$–$C_4$ monohaloalkyl, $C_1$–$C_2$ polyhaloalkyl and mono- or di-$C_1$–$C_4$) alkylamino;

(v) $R_5$ is selected from the group consisting of hydrogen, halogen, $C_1$–$C_5$ alkyl, $C_1$–$C_5$ alkoxy, $C_1$–$C_4$ monohaloalkyl, $C_1$–$C_2$ polyhaloalkyl, cyano and $C_1$–$C_8$ alkoxycarbonyl;

(vi) each $R_6$ is selected from the group consisting of halogen, $C_1$–$C_5$ alkyl, $C_1$–$C_4$ alkoxy, cyano, $C_1$–$C_8$ alkoxycarbonyl, $C_1$–$C_2$ polyhaloalkyl, $C_1$–$C_4$ monohaloalkyl, and mono- and di($C_1$–$C_4$)alkylamino; and (vii) e is an integer from 1 to 4, and c is an integer of form 0 to 2.

2. A compound according to claim 1 wherein ring B is fused to the e face of the six member ring of the indolino portion of the compound; $R_1$ is selected from the group consisting of $C_1$–$C_4$ alkyl, allyl, carboxy ($C_2$–$C_4$)alkyl, cyano($C_2$–$C_4$)alkyl, $C_1$–$C_4$ acyloxy($C_2$–$C_4$)alkyl, hydroxy($C_2$–$C_4$)alkyl, and $(C_2H_4O)_m CH_3$, wherein m is an integer of from 1 to 3; $R_2$ and $R_3$ are each selected from the group consisting of $C_1$–$C_5$ alkyl and phenyl; each $R_4$ is selected from the group consisting of $C_1$–$C_2$ alkyl, $C_1$–$C_2$ alkoxy, chloro, fluoro, bromo, nitro, trifluoromethyl and dimethylamino; $R_5$ is selected from the group consisting of hydrogen, $C_1$–$C_2$ alkyl, $C_1$–$C_2$ alkoxy, $C_1$–$C_2$ monohaloalkyl, fluoro and trifluoromethyl; each $R_6$ is selected from the group consisting of $C_1$–$C_2$ alkyl, $C_1$–$C_2$ alkoxy, chloro, fluoro, trifluoromethyl and mono- or di($C_1$-$C_4$)alkylamino; e is 1 or 2, and c is an integer of from 0 to 2.

3. A compound according to claim 2 wherein $R_1$ is a $C_1$-$C_4$ alkyl; $R_2$ and $R_3$ are each selected from the group consisting of methyl, ethyl and phenyl; each $R_4$ is selected from the group consisting of $C_1$-$C_2$ alkyl, $C_1$-$C_2$ alkoxy, chloro, fluoro, nitro, trifluoromethyl and dimethylamino; $R_5$ is hydrogen; each $R_6$ is selected from the group consisting of $C_1$-$C_2$ alkyl, $C_1$-$C_2$ alkoxy, chloro, fluoro, trifluoromethyl and mono- or di($C_1$-$C_4$)alkylamino; c is an integer of from 0 to 2 and e is 1 or 2.

4. 5′,7′-dimethoxy-1,1,3-trimethylspiro[benz[e]indolino-2,2′-[2H-1,4]benzoxazine].

5. A photochromic article comprising an organic host material containing a photochromic amount of a photochromic compound represented by the graphic formula:

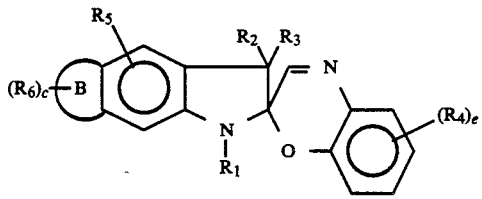

wherein:
(i) B is a benzene ring that is fused to the e,f, or g face of the six member ring of the indolino portion of the compound,
(ii) $R_1$ is selected from the group consisting of $C_1$-$C_8$ alkyl, phen($C_1$-$C_4$) alkyl, naphth($C_1$-$C_4$)alkyl, allyl, acrylyl, methacrylyl, carboxy($C_2$-$C_6$)alkyl, cyano($C_2$-$C_6$)alkyl, $C_1$-$C_4$ acyloxy($C_2$-$C_6$)alkyl, hydroxy($C_2$-$C_6$)alkyl, and ($C_2H_4O$)$_m$·$CH_3$, wherein m is an integer of from 1 to 6;
(iii) $R_2$ and $R_3$ are each selected from the group consisting of $C_1$-$C_5$ alkyl, phenyl, mono- and di- substituted phenyl, and phen($C_1$-$C_4$) alkyl, or combine to form an alicyclic ring containing from 6 to 8 carbon atoms (including the spiro carbon atom), said phenyl substituents being selected from $C_1$-$C_5$ alkyl and $C_1$-$C_5$ alkoxy;
(iv) each $R_4$ is selected from the group consisting of halogen, $C_1$-$C_5$ alkyl, $C_1$-$C_5$ alkoxy, nitro, cyano, thiocyano, $C_1$-$C_4$ monohaloalkyl, $C_1$-$C_2$ polyhaloalkyl and mono- or di($C_1$-$C_4$) alkylamino;
(v) $R_5$ is selected from the group consisting of hydrogen, halogen, $C_1$-$C_5$ alkyl, $C_1$-$C_5$ alkoxy, $C_1$-$C_4$ monohaloalkyl, $C_1$-$C_2$ polyhaloalkyl, cyano and $C_1$-$C_8$ alkoxycarbonyl;
(vi) each $R_6$ is selected from the group consisting of halogen, $C_1$-$C_5$ alkyl, $C_1$-$C_5$ alkoxy, cyano $C_1$-$C_8$ alkoxycarbonyl, $C_1$-$C_2$ polyhaloalkyl, $C_1$-$C_4$ monohaloalkyl, and mono- and di($C_1$-$C_4$)alkylamino; and
(vii) e is an integer from 1 to 4, and c is an integer of from 0 to 2.

6. The photochromic article of claim 5 wherein the transparent organic host material is selected from the group consisting essentially of polymers of polyol(allyl carbonate), polymers of polyfunctional acrylate monomers, polyacrylates, poly(alkylacrylates), cellulose acetate, cellulose triacetate, cellulose acetate propionate, cellulose acetate butyrate, poly(vinyl acetate), poly(vinyl alcohol), poly(vinyl chloride); poly(vinylidene chloride); polyurethanes, poly(ethylene terephthalate), polycarbonate, polystyrene, copoly(styrene-methylacrylate), a copoly(styrene-acrylonitrile), polyvinyl butyral, and homopolymers and copolymers of diallylidene pentaerythritol.

7. The photochromic article of claim 6 wherein the transparent host material is selected from poly[diethylene glycol bis(allyl carbonate)]and its copolymers with vinyl acetate.

8. The photochromic article of claim 6 wherein ring B is fused to the e face of the six member ring of the indolino portion of the compound; $R_1$ is selected from the group consisting of $C_1$-$C_4$ alkyl, allyl, carboxy ($C_2$-$C_4$)alkyl, cyano($C_2$-$C_4$)alkyl, $C_1$-$C_4$ acyloxy(C-2-$C_4$)alkyl, hydroxy($C_2$-$C_4$)alkyl, and ($C_2H_4O$)$_m$·$CH_3$, wherein m is an integer of from 1 to 3; $R_2$ and $R_3$ are each selected from the group consisting of $C_1$-$C_5$ alkyl and phenyl; each $R_4$ is selected from the group consisting of $C_1$-$C_2$ alkyl, $C_1$-$C_2$ alkoxy, chloro, fluoro, bromo, nitro, trifluoromethyl and dimethylamino; $R_5$ is selected from the group consisting of hydrogen, $C_1$-$C_2$ alkyl, $C_1$-$C_2$ alkoxy, $C_1$-$C_2$ monohaloalkyl, fluoro and trifluoromethyl; each $R_6$ is selected from the group consisting of $C_1$-$C_2$ alkyl, $C_1$-$C_2$ alkoxy, chloro, fluoro, trifluoromethyl and mono- or di($C_1$-$C_4$)alkylamino; e is 1 or 2, and c is 0 to 2.

9. A photochromic article comprising a solid transparent polymerized organic host material selected from the group consisting of homopolymers and copolymers of diethylene glycol bis(allyl carbonate), polyacrylates, poly(alkylacrylates), homopolymers and copolymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate), polystyrene, copoly(styrene-methylmethacrylate), copoly(styrene-acrylonitrile), polyvinylbutyral, and homopolymers and copolymers of diallylidene pentaerythritol, said host material containing a photochromic amount of a photochromic compound represented by the graphic formula:

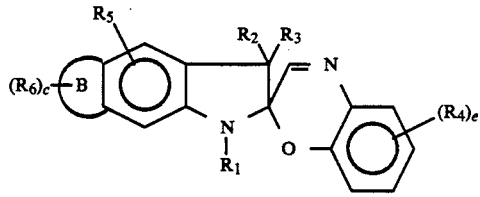

wherein:
(i) B is a benzene ring that is fused to the e face of the six member ring of the indolino portion of the compound,
(ii) $R_1$ is a $C_1$-$C_4$ alkyl;
(iii) $R_2$ and $R_3$ are each selected from the group consisting of methyl, ethyl and phenyl;
(iv) each $R_4$ is selected from the group consisting of $C_1$-$C_2$ alkyl, $C_1$-$C_2$ alkoxy, chloro, fluoro, nitro, trifluoromethyl, and dimethylamino;
(v) $R_5$ is hydrogen;
(vi) each $R_6$ is selected from the group consisting of $C_1$-$C_2$ alkyl, $C_1$-$C_2$ alkoxy, chloro, fluoro, trifluoromethyl and mono- or di-($C_1$-$C_4$) alkylamino; and
(vii) c is an integer of from 0 to 2 and e is 1 or 2.

10. The photochromic article of claim 9 wherein the host material is prepared from homopolymers and copolymers of diethylene glycol bis(allyl carbonate).

11. The photochromic article of claim 10 wherein the photochromic compound is present in amounts of from 0.05 to 10 weight percent.

12. The photochromic article of claim 11 wherein the article is an optical element.

13. The photochromic article of claim 12 wherein the optical element is a lens.

14. The photochromic article of claim 13 wherein the lens is an ophthalmic lens.

15. 5',7'-dimethoxy-1,3,3-trimethylspiro[benz[g]indolino-2,2'-[2H-1,4]benzoxazine].

16. A compound represented by one of the following graphic formulae:

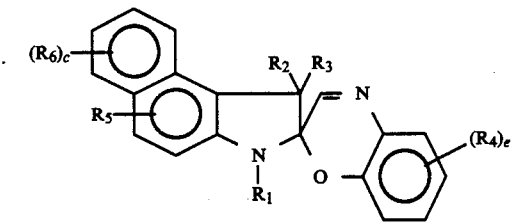

-continued

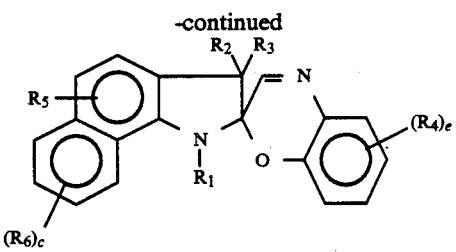

wherein $R_1$ is selected from the group consisting of $C_1$–$C_4$ alkyl, cyano($C_2$–$C_4$) alkyl and $C_1$–$C_4$ acyloxy($C_2$–$C_4$)alkyl; $R_2$ and $R_3$ are each selected from the group consisting of methyl, ethyl and propyl; $R_4$ is methoxy; $R_5$ is selected from the group consisting of hydrogen, halogen, $C_1$–$C_5$ alkyl, $C_1$–$C_5$ alkoxy, $C_1$–$C_5$ monohaloalkyl, $C_1$–$C_2$ polyhaloalkyl, cyano and $C_1$–$C_8$ alkoxycarbonyl; each $R_6$ is selected from the group consisting of halogen, $C_1$–$C_5$ alkyl, $C_1$–$C_5$ alkoxy, cyano, $C_1$–$C_8$ alkoxycarbonyl $C_1$–$C_2$ polyhaloalkyl, $C_1$–$C_4$ monohaloalkyl and mono- and di($C_1$–$C_4$) alkylamino; and e is 1 or 2 and c is an integer of from 0 to 2.

17. A compound according to claim 16 wherein $R_4$ is located at the 5' or 7' position when e is 1 and at the 5' and 7' positions when e is 2.

18. A compound according to claim 17 wherein $R_5$ is selected from the group consisting of hydrogen, $C_1$–$C_2$ alkyl, $C_1$–$C_2$ alkoxy, $C_1$–$C_2$ monohaloalkyl, fluoro and trifluoromethyl; each $R_6$ is selected from the group consisting of $C_1$–$C_2$ alkyl, $C_1$–$C_2$ alkoxy, chloro, fluoro, trifluoromethyl and mono- or di($C_1$–$C_4$) alkylamino; e is 1 or 2 and c is an integer of from 0 to 2.

19. A compound according to claim 17 wherein $R_5$ is hydrogen; each $R_6$ is selected from the group consisting of $C_1$–$C_2$ alkyl, $C_1$–$C_2$ alkoxy, chloro, fluoro, trifluoromethyl and mono- or di($C_1$–$C_4$)alkylamino; e is 1 or 2 and c is an integer of from 0 to 2.

* * * * *

UNITED STATES PATENT AND TRADEMARK OFFICE
CERTIFICATE OF CORRECTION

PATENT NO. : 4,936,995
DATED : June 26, 1990
INVENTOR(S) : Patricia L. Kwiatkowski It is certified that error appears in the above-identified patent and that said Letters Patent is hereby corrected as shown below:

Claim 1, column 14, line 38, "allyl" should be --alkyl--;
Claim 1, column 14, line 53, "form" should be --from--.

Claim 16, column 18, lines 13-14, "$C_2-C_4$" should be --$C_2-C_4$--.

Claim 16, lines 17-19, "$C_1 14 C_5$ alkoxy, $C_1-C_5$ monohaloalkyl, $C_1-C_2$ polyhaloalkyl, cyano and $C_1-C_8$ alkoxycarbonyl" should be --$C_1-C_5$ alkoxy, $C_1-C_4$ monohaloalkyl, $C_1-C_2$ polyhaloalkyl, cyano and $C_1-C_8$ alkoxycarbonyl--.

Signed and Sealed this

Nineteenth Day of November, 1991

*Attest:*

HARRY F. MANBECK, JR.

*Attesting Officer*   *Commissioner of Patents and Trademarks*